United States Patent [19]

Bartmann et al.

[11] Patent Number: 5,589,102
[45] Date of Patent: Dec. 31, 1996

[54] BENZENE DERIVATIVES, AND LIQUID-CRYSTALLINE MEDIUM

[75] Inventors: Ekkehard Bartmann, Erzhausen; Kazuaki Tarumi, Seeheim, both of Germany

[73] Assignee: Merck Patent Gesellschaft mit beschrankter Haftung, Germany

[21] Appl. No.: 523,240

[22] Filed: Sep. 5, 1995

[30] Foreign Application Priority Data

Sep. 6, 1994 [DE] Germany .......................... 44 31 737.9

[51] Int. Cl.$^6$ ................... C09K 19/52; C09K 19/30; C07C 25/13; G02F 1/13
[52] U.S. Cl. ..................... 252/299.01; 252/299.61; 252/299.62; 252/299.63; 252/299.66; 570/127; 570/131; 570/141; 570/142; 570/144; 570/182; 349/182
[58] Field of Search .................. 252/299.01, 299.61, 252/299.62, 299.63, 299.66; 570/127, 131, 141, 142, 144, 182; 359/103

[56] References Cited

U.S. PATENT DOCUMENTS 5,045,229  9/1991  Bartmann et al. ............... 252/299.01

*Primary Examiner*—Shean Wu
*Attorney, Agent, or Firm*—Millen, White, Zelano & Branigan, P.C.

[57] ABSTRACT

Benzene derivatives of the formula I

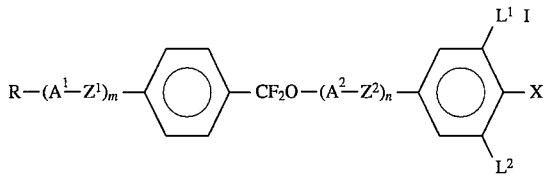

in which R, $A^1$, $A^2$ X, $L^1$, $L^2$ m and n are as defined in claim are suitable as components of liquid-crystalline media.

17 Claims, No Drawings

BENZENE DERIVATIVES, AND LIQUID-CRYSTALLINE MEDIUM

SUMMARY OF THE INVENTION

The invention relates to benzene derivatives of the formula I

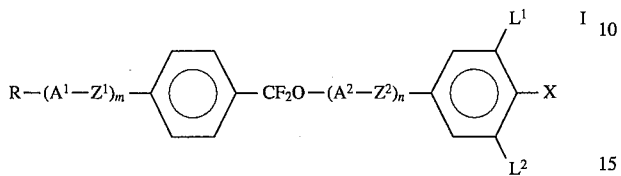

in which

R is an alkyl or alkenyl radical having 1 to 15 carbon atoms which is unsubstituted, monosubstituted by CN or $CF_3$ or at least monosubstituted by halogen, wherein one or more (e.g., up to 5, preferably 1 or 2) $CH_2$ groups in these radicals may also, in each case independently of one another, be replaced by —O—, —S—,

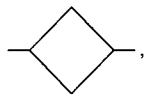

—CO—, —CO—O—, —O—CO— or —O—CO—O— in such a way that O atoms are not linked directly to one another, $A^1$ and $A^2$ are each, independently of one another, (a) a trans-1,4-cyclohexylene radical in which, in addition, one or more (e.g. 1–2) nonadjacent $CH_2$ groups may be replaced by —O— and/or —S—, (b) a 1,4-phenylene radical in which, in addition, one or two CH groups may be replaced by N, (c) 1,4-cyclohexenylene, (d) a radical from the group consisting of 1,4-bicyclo[2.2.2]octylene, piperidine- 1,4-diyl, naphthalene-2,6-diyl, decahydronaphthalene-2,6-diyl and 1,2,3,4-tetrahydronaphthalene-2,6-diyl, where the radicals (a) to (c) may be monosubstituted or polysubstituted, e.g., 1–3 times, preferably 1–2 times, by CN or fluorine, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, or one of the radicals $Z^1$ and $Z^2$ is alternatively —$(CH_2)_4$— or —CH=CH—$CH_2CH_2$—, $L^1$ and $L^2$ are each, independently of one another, H or F, m and n are each, independently of one another, 0 or 1, and is F, Cl, halogenated alkyl, alkoxy or alkenyl having 1 to 6 carbon atoms.

The invention furthermore relates to the use of these compounds as components of liquid-crystalline media and to liquid-crystal and electro-optical display elements containing the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

The invention has as an object finding novel, stable, liquid-crystalline or mesogenic compounds which are suitable as components of liquid-crystalline media and in particular simultaneously have relatively low viscosity and relatively high dielectric anisotropy.

It has now been found that compounds of the formula I are eminently suitable as components of liquid-crystalline media. In particular, they have relatively low viscosities. They can be used to obtain stable liquid-crystalline media having a broad mesophase range and advantageous values for the optical and dielectric anisotropy. These media furthermore have very good low-temperature behavior.

Liquid crystals containing difluoromethylene bridges, such as, for example, compounds of the formula

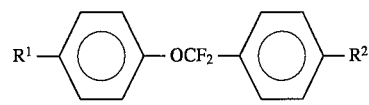

$R^1$ and $R^2$ = alkyl have already been disclosed in DE 40 23 106, which corresponds to U.S. Pat. No. 5,266,085. However, the compounds of the present invention are not described therein.

In view of the wide variety of areas of application of such compounds having low Δn and high Δε, however, it was desirable to have available further compounds which have properties precisely customized to the particular applications.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominently composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystal display elements, in particular electro-optical display elements, containing such media.

For reasons of simplicity, $A^4$ below denotes a radical of the formula

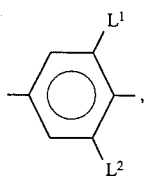

Cyc denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo[2.2.2]octylene radical, where Cyc and/or Phe may be unsubstituted or monosubstituted or disubstituted by F or CN.

$A^1$ and $A^2$ are preferably selected from the group consisting of Cyc, Che, Phe, Pyr, Pyd and Dio, where, preferably, only one of the radicals $A^1$ and $A^2$ present in the molecule is Che, Phe, Pyr, Pyd or Dio.

Accordingly, the compounds of the formula I cover bicyclic compounds of the sub-formula Ia R-Phe-CF$_2$-O-A$^4$-X     Ia tricyclic compounds of the sub-formulae Ib to Ie R-A$^1$-Phe-CF$_2$-O-A$^4$-X     Ib R-A$^1$-Z$^1$-Phe-CF$_2$-O-A$^4$-X     Ic R-Phe-CF$_2$-O-A$^2$-A$^4$-X     Id R-Phe-CF$_2$-O-A$^2$-Z$^2$-A$^4$-X     Ie tetracyclic compounds of the sub-formulae If to Ii R-A$^1$-Phe-CF$_2$-O-A$^2$-A$^4$-X     If R-A$^1$-Z$^1$-Phe-CF$_2$-O-A$^2$-A$^4$-X     Ig R-A$^1$-Z$^1$-Phe-CF$_2$-O-A$^2$-Z$^2$-A$^4$-X     Ih R-A$^1$-Phe-CF$_2$-O-A$^2$-Z$^2$-A$^4$-X     Ii The compounds of the formula I preferably contain two or three rings; compounds of the formulae Ib to Ie are particularly preferred.

The preferred compounds of the sub-formula are those of the sub-formulae

R-Phe-Z$^1$-Phe-CF$_2$-O-A$^4$-X     Ica

R-Cyc-Z$^1$-Phe-CF$_2$-O-A$^4$-X     Icb

R-Pyd-Z$^1$-Phe-CF$_2$-O-A$^4$-X     Icc

R-Pyr-Z$^1$-Phe-CF$_2$-O-A$^4$-X     Icd

R-Dio-Z$^1$-Phe-CF$_2$-O-A$^4$-X     Ice

R-Che-Z$^1$-Phe-CF$_2$-O-A$^4$-X     Icf

Of these, those of the formulae Ica and Icb are particularly preferred.

The preferred compounds of the sub-formula Ie are those of the sub-formulae

R-Phe-CF$_2$-O-Phe-Z$^2$-A$^4$-X     Iea

R-Phe-CF$_2$-O-Cyc-Z$^2$-A$^4$-X     Ieb

R-Phe-CF$_2$-O-Pyd-Z$^2$-A$^4$-X     Iec

R-Phe-CF$_2$-O-Pyr-Z$^2$-A$^4$-X     Ied

R-Phe-CF$_2$-O-Dio-Z$^2$-A$^4$-X     Ief

R-Phe-CF$_2$-O-Che-Z$^2$-A$^4$-X     Iee

In the compounds of the formulae above and below, X has 1, 2, 3, 4, 5, 6 or 7 halo atoms where it is halogenated alkyl, up to perhalo, and is preferably F, Cl, CF$_3$, OCF$_3$, OCHF$_2$, OCH$_2$F, CF$_2$H, CF$_2$Cl, OCF$_2$Cl, OCHFCF$_3$, OC$_2$F$_4$H, OC$_2$F$_5$, OC$_3$F$_7$, OCH$_2$CF$_2$H, OCF$_2$CH$_2$CF$_3$, OCH$_2$CF$_3$, OCF$_2$CHFCF$_3$, OCH$_2$CF$_2$H, CHFCF$_2$H, CH$_2$CH$_2$F, OCH$_2$CH$_2$CF$_3$, CH$_2$CF$_3$, OCF=CF$_2$, OCH=CF$_2$, OCH=CFH, CF=CF$_2$, CH=CF$_2$, OCF=CF—CF$_3$, in particular F, Cl, OCF$_3$, OCH$_2$F, CF$_3$, OCH$_2$CHF$_2$, OC$_2$F$_5$, OC$_3$F$_7$, OCHFCF$_3$ and OCH=CF$_2$. X preferably contains not more than 3 carbon atoms.

R is preferably alkyl, furthermore alkoxy. $A^1$ and/or $A^2$ are preferably Phe, Cyc, Che, Pyr or Dio. The compounds of the formula I preferably contain not more than one of the radicals Bi, Pyd, Pyr, Dio and Dit.

Preference is also given to compounds of the formula I and of all sub-formulae in which $A^1$ and/or $A^2$ is/are 1,4-phenylene which is monosubstituted or disubstituted by F or monosubstituted by CN. These are in particular 2-fluoro-1,4-phenylene, 3-fluoro-1,4-phenylene, 3,5-difluoro-1,4-phenylene, 2-cyano-1,4-phenylene and 3-cyano-1,4-phenylene.

Preference is furthermore given to compounds of the formula I in which $L^1$ and/or $L^2$ are fluorine. In particular in the compounds of the formula I in which X is F, Cl or OCF$_3$, $L^1$ and/or $L^2$ is/are preferably fluorine.

$Z^1$ and $Z^2$ are preferably a single bond or —CH$_2$CH$_2$—, secondarily preferably —CH$_2$—O— or —OCH$_2$—.

If one of the radicals $Z^1$ and $Z^2$ is —(CH$_2$)$_4$— or —CH=CH—CH$_2$CH$_2$—, the other radical $Z^1$ or $Z^2$ (if present) is preferably a single bond.

If R is an alkyl radical in which one CH$_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one CH$_2$ group has been replaced by —O— and one has been replaced by —CO—, these are preferably adjacent. This thus contains an acyloxy group —CO—O— or an oxycarbonyl group —O—CO—. It is preferably straight-chain and has 2 to 6 carbon atoms.

It is accordingly in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one CH$_2$ group has been replaced by unsubstituted or substituted —CH=CH— and an adjacent CH$_2$ group has been replaced by CO or CO—O or O—CO, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or CF$_3$, this radical is preferably straight-chain and the substitution by CN or CF$_3$ is in the ω-position.

If R is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance owing to better solubility in the customary liquid-crystalline base materials, in particular as chiral dopants if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more CH$_2$ groups have been replaced by —O— and/or —CO—O—, this can be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl and 5,5-bis(ethoxycarbonyl)hexyl.

Compounds of the formula I which contain wing groups R which are suitable for polycondensation reactions are suitable for the preparation of liquid-crystalline polycondensates.

The formula I covers both the racemates of these compounds and the optical antipodes, and mixtures thereof.

Of these compounds of the formula I and of the sub-formulae, preference is given to those in which at least one of the radicals present therein has one of the preferred meanings given.

In the compounds of the formula I, preferred stereoisomers are those in which the rings Cyc and piperidine are trans-1,4-disubstituted. Those of the abovementioned formulae which contain one or more groups Pyd, Pyr and/or Dio in each case cover the two 2,5-positional isomers.

A very particularly preferred smaller group of compounds comprises those of the sub-formulae I1 to I8 (L$^1$, L$^2$ and L$^3$=H or F):

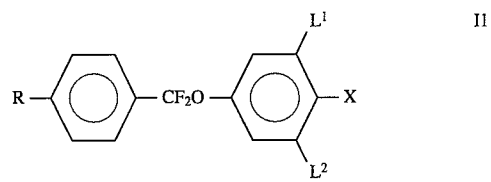

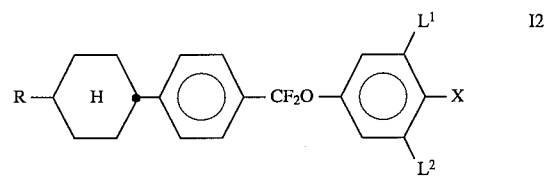

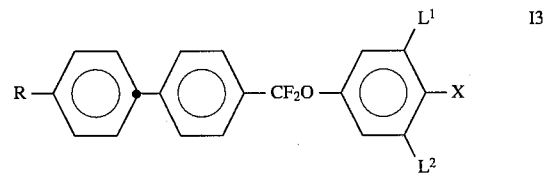

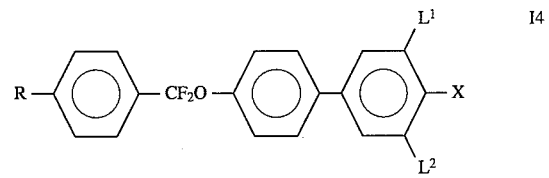

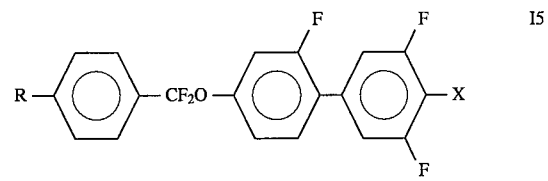

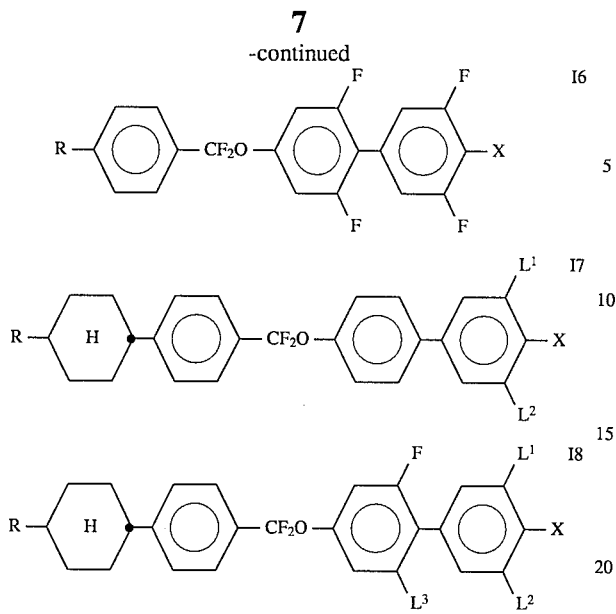

Particular preference is given to compounds of the formula I2.

All of the compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions, from starting materials which are known or conventinally preparable.

Use may also be made here of variants which are known per se, but are not mentioned here in greater detail.

The novel compounds can be prepared, for example, by reacting benzene derivatives in accordance with the reaction schemes below:

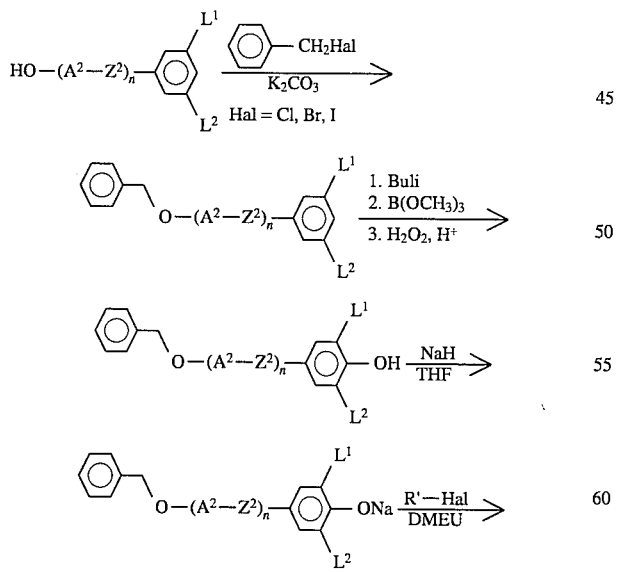

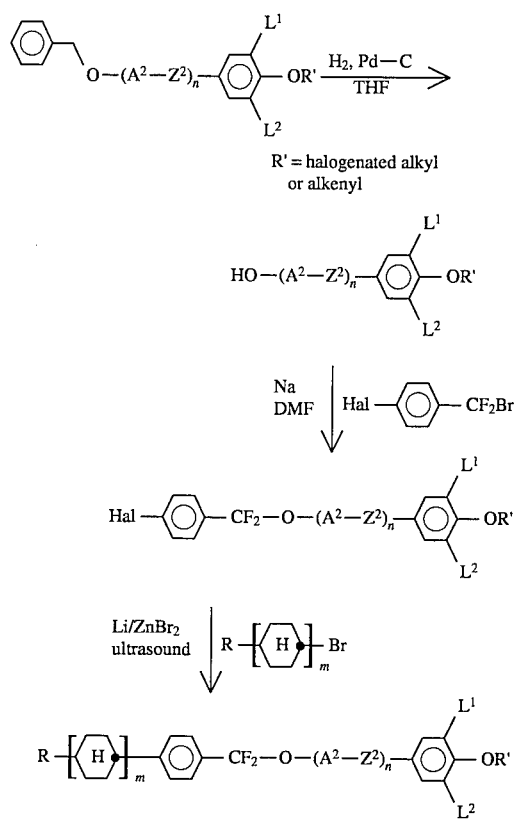

Scheme 2
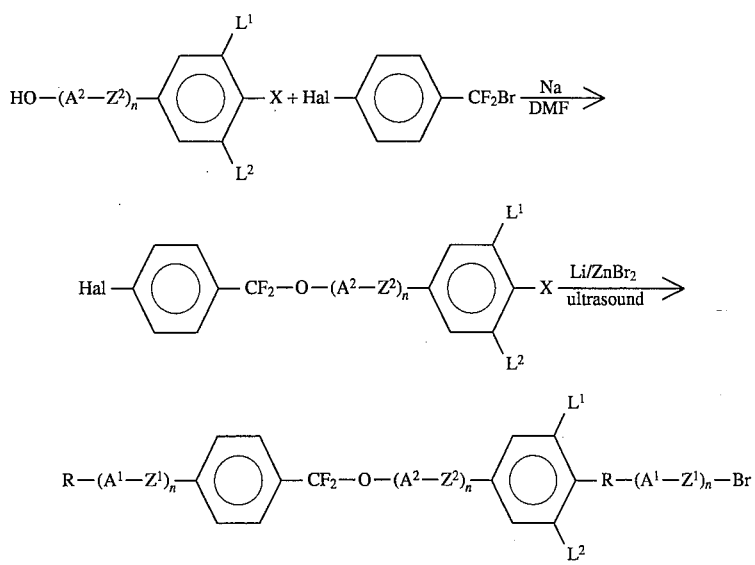
The synthesis of some particularly preferred compounds is described below:
Scheme 3
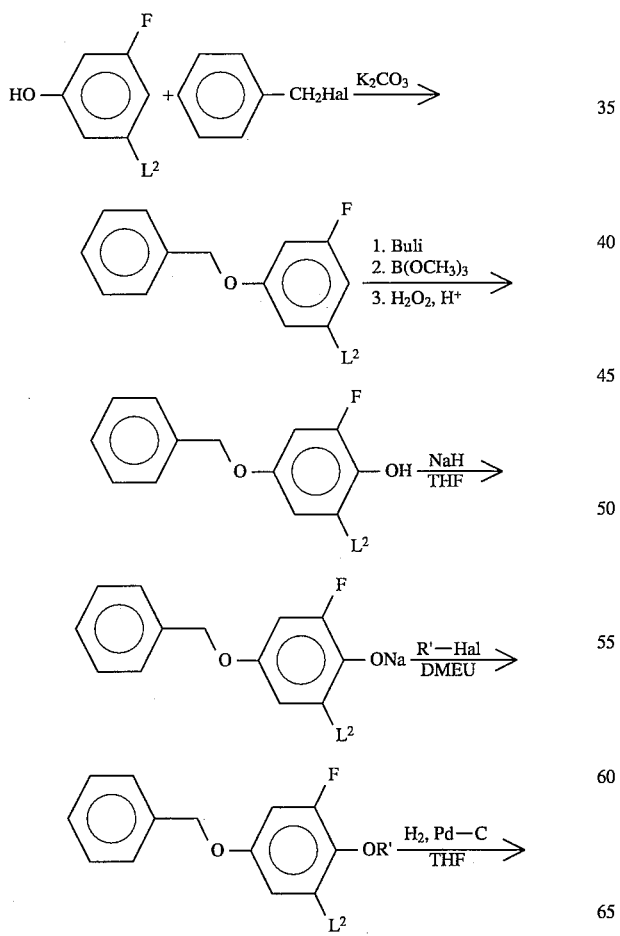
-continued
Scheme 3
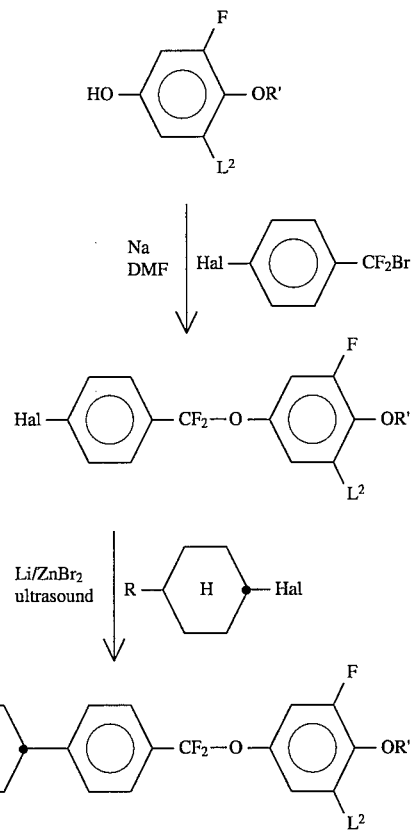

Scheme 4

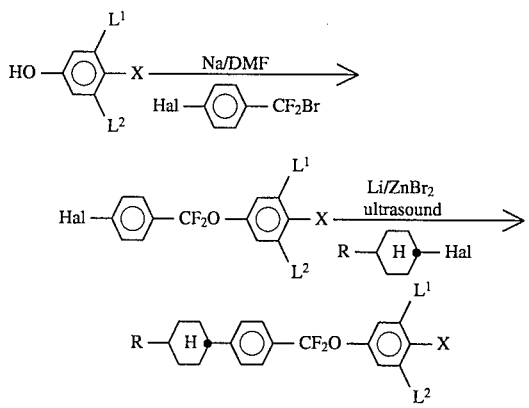

The liquid-crystalline media according to the invention preferably comprise 2 to 40, in particular 4 to 30, components as further constituents besides one or more compounds according to the invention. These media very particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl-or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_1$, where i is 0 or 1, and k+1 is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5 to 90% and in particular 10% to 90%.

The media according to the invention preferably comprise 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention. Preferred media do not contain more than 10% by weight of cyano-containing compounds.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n or m carbon atoms respectively. The coding in Table B is self-evident. In Table A, only the acronym for the parent structure is given. In individual cases, a code follows for the substituents $R^1$, $R^2$, $L^1$ and $L^2$, separated from the acronym for the parent structure by a hyphen:

| Code for $R^1$, $R^2$ $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| nT | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |

TABLE A

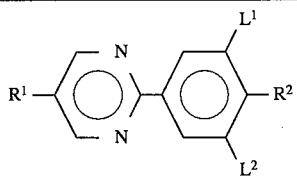

PYP

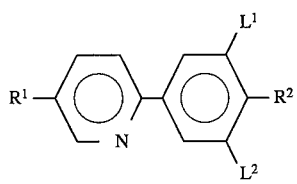

PYRP

TABLE A-continued

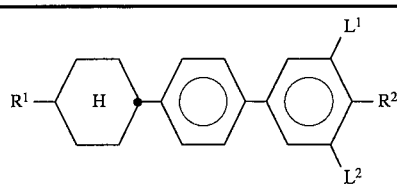

BCH

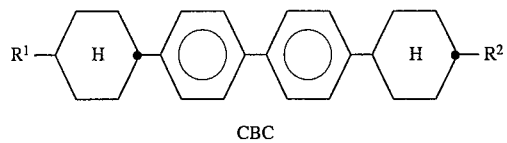

CBC

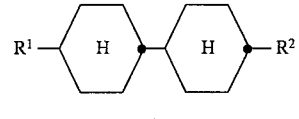

CCH

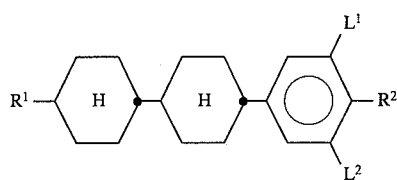

CCP

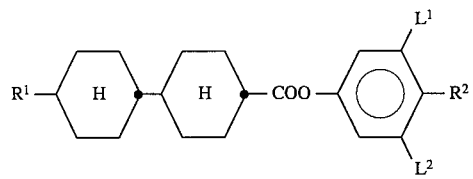

CP

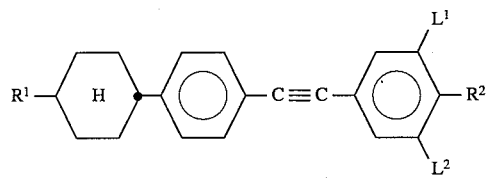

CPTP

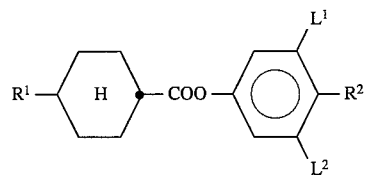

D

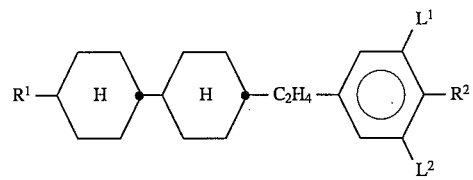

ECCP

TABLE A-continued
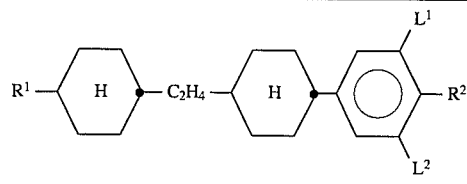
CECP
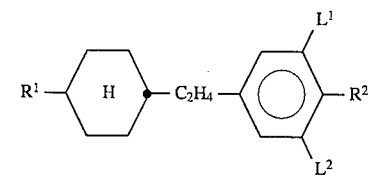
EPCH
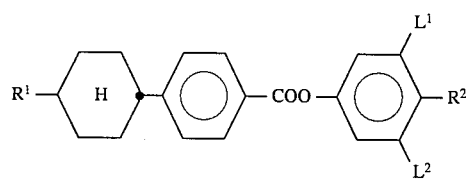
HP
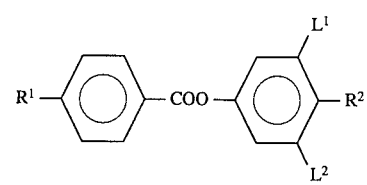
ME
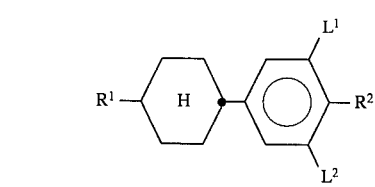
PCH
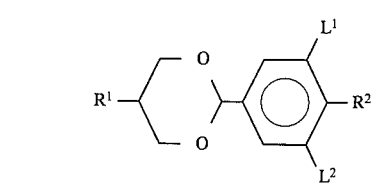
PDX
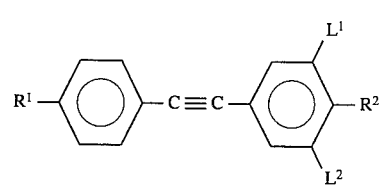
PTP
TABLE A-continued
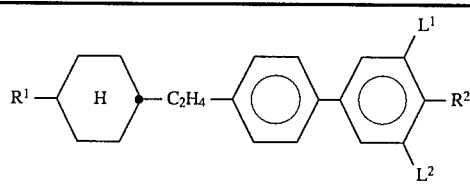
BECH
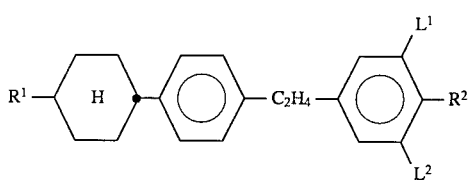
EBCH
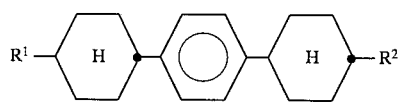
CPC
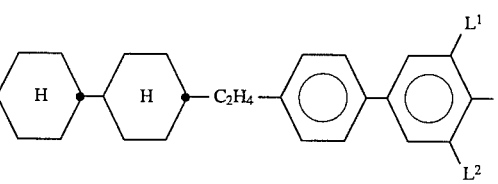
CCEB
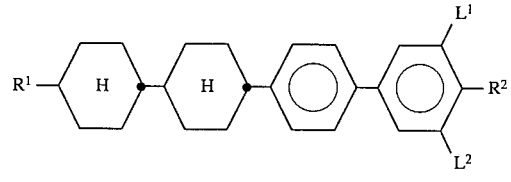
CCB
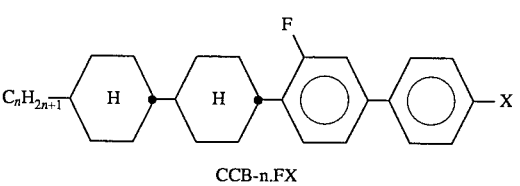
CCB-n.FX
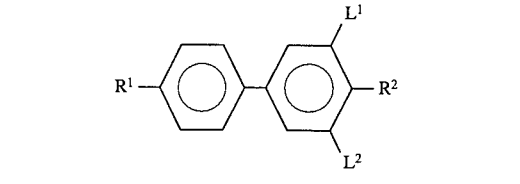
B
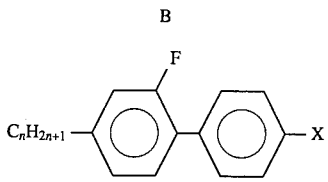
B-n.FX

TABLE B

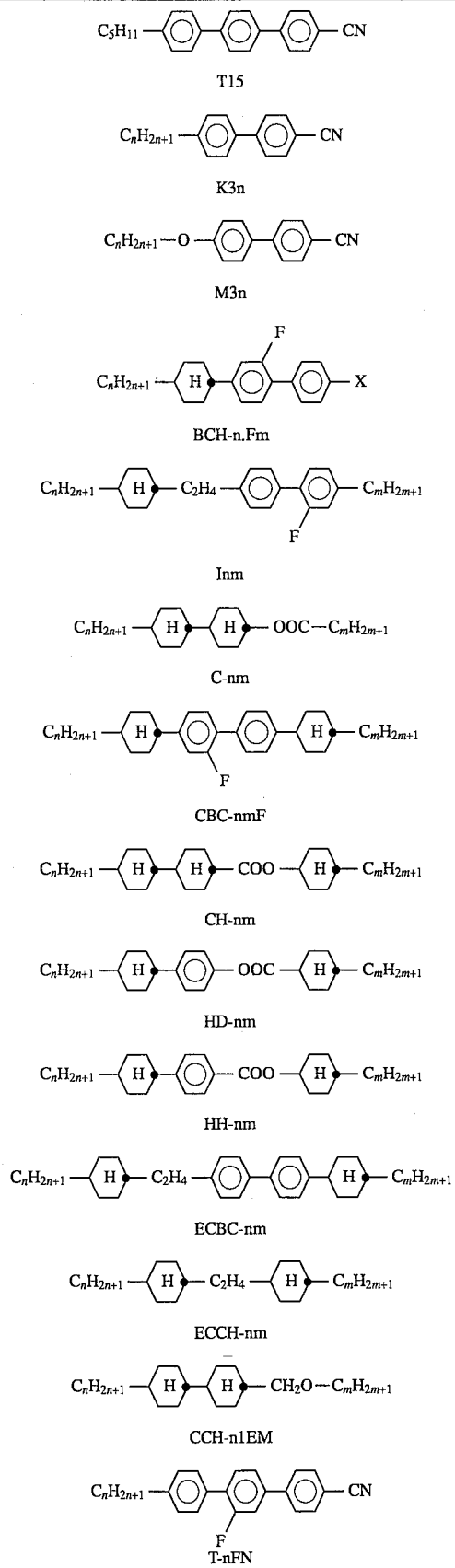

T15, K3n, M3n, BCH-n.Fm, Inm, C-nm, CBC-nmF, CH-nm, HD-nm, HH-nm, ECBC-nm, ECCH-nm, CCH-n1EM, T-nFN

TABLE B-continued

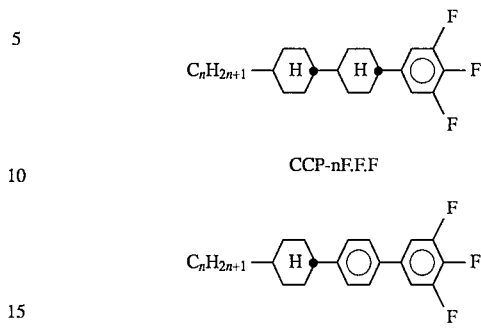

CCP-nF.F.F, BCH-nF.F.F

The entire disclosure of all applications, patents and publications, cited above and below, and of corresponding German Application No. P 44 31 737.9, filed Sep. 6, 1994, are hereby incorporated by reference.

In the foregoing and in the following examples, all temperatures are set forth uncorrected in degrees Celsius; and, unless otherwise indicated, all parts and percentages are by weight. In addition, mp. denotes melting point, cp.= clearing point. Furthermore, C=crystalline state, N=nematic phase, S=smectic phase and I=isotropic phase. The data between these symbols represent the transition temperatures. $\Delta n$ denotes the optical anisotropy (589 nm, 20° C.), and the viscosity ($mm^2$/sec) was determined at 20° C.

"Conventional work-up" means that water is added if appropriate, the mixture is extracted with dichloromethane, methyl tert-butyl ether, diethyl ether or toluene, the organic phase is separated off, dried and evaporated, and the product is purified by distillation under reduced pressure or crystallization and/or chromatography. The following abbreviations are used:

| | |
|---|---|
| BuLi | butyllithium |
| DAST | diethylaminosulphur trifluoride |
| DCC | dicyclohexylcarbodiimide |
| DIBALH | diisobutylaluminium hydride |
| DMEU | 1,3-dimethyl-2-imidazolidinone |
| DMF | N,N-dimethylformamide |
| POT | potassium tert-butoxide |
| THF | tetrahydrofuran |
| pTsOH | p-toluenesulphonic acid |
| TMEDA | tetramethylethylenediamine |

EXAMPLES

Example 1

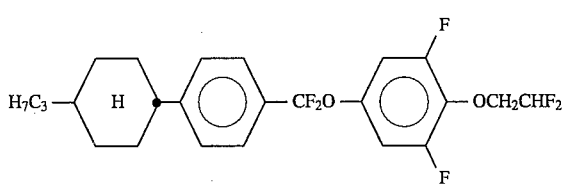

Step 1.1

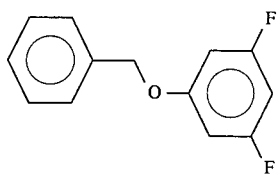 I 2.2 mol of benzyl bromide are added to 2.0 mol of 3,5-difluorobenzene, 2.2 mol of potassium carbonate and 1000 ml of methyl ethyl ketone. The mixture is stirred at 70° C. for 10 hours and allowed to cool, and the resultant precipitate is filtered off with suction. The filtrate is evaporated and purified by fractional vacuum distillation. 138°–142° C./5 mbar.

Step 1.2

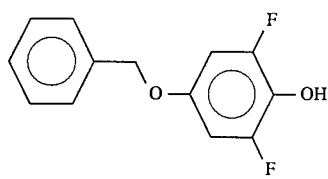 II 1.55 mol of BuLi (15% in n-hexane) are added dropwise under a nitrogen atomsphere to 1.55 mol of diisopropylamine in 50 ml of THF at −25° C. The solution is stirred at −25° C. for 45 minutes and added dropwise to the solution, cooled to −75° C., of 1.55 mol of I and 3 l of THF. The mixture is stirred at −75° C. for 1 hour, 1.55 mol of trimethyl borate are added, and the mixture is stirred at −75° C. for 1 hour. The mixture is allowed to warm to −30° C., 175 ml of glacial acetic acid and then 65 ml of conc. $H_2SO_4$ are added, and the mixture is stirred at 30° C. for a further hour. After addition of 1.5 mol of $H_2O_2$ (35%), the mixture is hydrolysed and stirred at 55° C. for 2 hours. The mixture is allowed to cool to room temperature, and the organic phase is separated off and subjected to conventional work-up.

Step 1.3

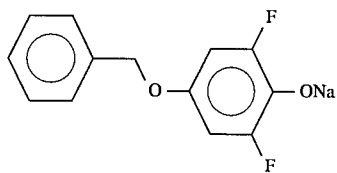 III 1.0 mol of sodium hydride (60%) is suspended in 300 ml of THF, and 1.0 mol of II in 300 ml of THF is added at 5° C. The mixture is stirred at room temperature for 1 hour, the residue is filtered off, and the filtrate is evaporated. After addition of 1000 ml of n-hexane, the mixture is stirred at 5° C. for 0.5 hour and evaporated. The crystals are dried in vacuo overnight.

Step 1.4

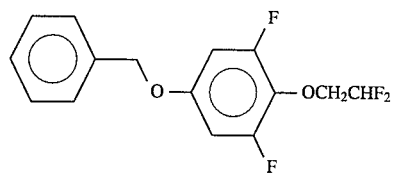 IV 0.95 mol of III are dissolved in 650 ml of DMEU and heated to 70° C. 1.0 mol of 2-bromo-1,1-difluoroethane is added dropwise with stirring, and the mixture is subsequently stirred at 70° C. for a further 5 hours. The reaction solution is poured into water, and the product is extracted with methyl tert-butyl ether and finally subjected to customary work-up.

Step 1.5

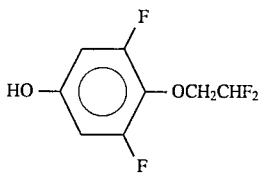 V 0.2 mol of IV are dissolved in 500 ml of THF, 10 g of Pd/C (5%) are added, and the mixture is hydrogenated. The mixture is subsequently filtered, evaporated and vacuum-distilled. bp. 120° C./5 mbar.

Step 1.6

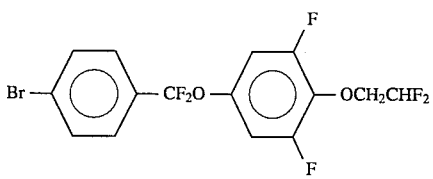 VI 0.08 mol of sodium is added to 0.08 mol of 1-(difluorobromomethyl)-4-bromobenzene in 500 ml of DMF. After the reaction mixture has been stirred for 0.5 hour, 0.039 mol of V is added. The mixture is stirred at 80° C. overnight and allowed to cool to room temperature, water is added, and the mixture is extracted with methyl tert-butyl ether. The combined organic extracts are subsequently subjected to customary work-up.

Step 1.7

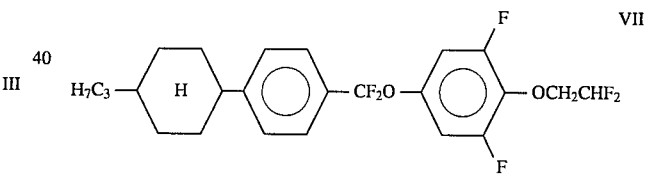 VII 0.1 mol of 4-transpropylcyclohexyl bromide, 0.05 mol of zinc bromide, 0.2 mol of lithium granules and 150 ml of toluene/THF (4:1) are introduced into a flask under a protective gas and treated with ultrasound for 15 minutes with stirring. 0.018 mol of VI and 1.4 g of tetrakis(triphenylphosphine)palladium(0) are added, and the mixture is stirred at room temperature for 72 hours. A saturated ammonium chloride solution is added, and the mixture is stirred for a further 15 minutes and then subjected to customary work-up. C 50 N 60.3 I; Δn=0.106; Δε=10.59.

The following compounds of the formula

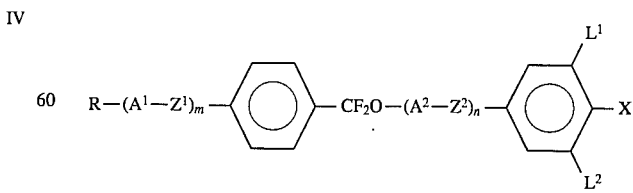

are prepared analogously:

| R | —(A¹—Z¹)ₘ— | —(A²—Z²)ₙ— | X | L¹ | L² |
|---|---|---|---|---|---|
| CH₃ | —⟨Cy-H⟩— | — | OCH₂CHF₂ | H | F |
| C₂H₅ | —⟨Cy-H⟩— | — | OCH₂CHF₂ | H | H |
| C₂H₅ | —⟨Cy-H⟩— | — | OCH₂CHF₂ | H | F |
| C₂H₅ | —⟨Cy-H⟩— | — | OCH₂CHF₂ | F | F |
| n-C₃H₇ | —⟨Cy-H⟩— | — | OCH₂CHF₂ | H | H |
| n-C₃H₇ | —⟨Cy-H⟩— | — | OCH₂CHF₂ | H | F |
| n-C₅H₁₁ | —⟨Cy-H⟩— | — | OCH₂CHF₂ | H | H |
| n-C₅H₁₁ | —⟨Cy-H⟩— | — | OCH₂CHF₂ | H | F |
| n-C₅H₁₁ | —⟨Cy-H⟩— | — | OCH₂CHF₂ | F | F |
| n-C₃H₇ | —⟨Ph⟩— | — | OCH₂CHF₂ | H | H |
| n-C₃H₇ | —⟨Ph⟩— | — | OCH₂CHF₂ | H | F |
| n-C₃H₇ | —⟨Ph⟩— | — | OCH₂CHF₂ | F | F |
| n-C₅H₁₁ | — | —⟨Ph⟩— | OCH₂CHF₂ | H | H |
| n-C₅H₁₁ | — | —⟨Ph-F⟩— | OCH₂CHF₂ | H | F |

-continued

| R | $-(A^1-Z^1)_m-$ | $-(A^2-Z^2)_n-$ | X | $L^1$ | $L^2$ |
|---|---|---|---|---|---|
| n-$C_5H_{11}$ | — | ![benzene with 2F] | $OCH_2CHF_2$ | F | F |
| n-$C_3H_7$ | — | — | $OCH_2CHF_2$ | H | H |
| n-$C_3H_7$ | — | — | $OCH_2CHF_2$ | H | F |
| n-$C_3H_7$ | — | — | $OCH_2CHF_2$ | F | F |
| n-$C_5H_{11}$ | — | — | $OCH_2CHF_2$ | H | H |
| n-$C_5H_{11}$ | — | — | $OCH_2CHF_2$ | H | F |
| n-$C_5H_{11}$ | — | — | $OCH_2CHF_2$ | F | F |
| $OC_2H_5$ | — | — | $OCH_2CHF_2$ | H | H |
| $OC_2H_5$ | — | — | $OCH_2CHF_2$ | H | F |
| $OC_2H_5$ | — | — | $OCH_2CHF_2$ | F | F |

Example 2

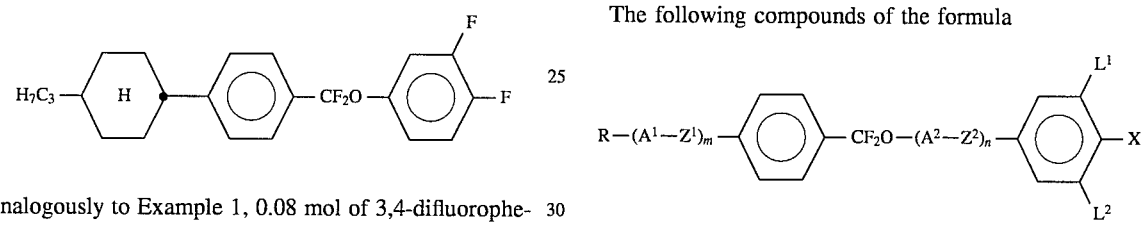

Analogously to Example 1, 0.08 mol of 3,4-difluorophenol are reacted first with 0.16 mol of 1-(difluorobromomethyl)-4-bromobenzene and subsequently with 4-trans-propylcyclohexyl bromide. C 67 N (48.1) I; $\Delta n=0.093$, $\Delta\epsilon=8.7$.

The following compounds of the formula $$R-(A^1-Z^1)_m-\bigcirc-CF_2O-(A^2-Z^2)_n-\bigcirc\begin{smallmatrix}L^1\\X\\L^2\end{smallmatrix}$$

are prepared analogously:

| R | $-(A^1-Z^1)_m-$ | $-(A^2-Z^2)_n-$ | X | $L^1$ | $L^2$ | |
|---|---|---|---|---|---|---|
| $CH_3$ | cyclohexyl-H | — | F | F | F | |
| $C_2H_5$ | cyclohexyl-H | — | F | H | H | |
| $C_2H_5$ | cyclohexyl-H | — | F | H | F | |
| $C_2H_5$ | cyclohexyl-H | — | F | F | F | |
| n-$C_3H_7$ | cyclohexyl-H | — | F | H | F | |
| n-$C_3H_7$ | cyclohexyl-H | — | F | F | F | C71 I; $\Delta n=+0.097$; $\Delta\epsilon=10.2$ |
| n-$C_5H_{11}$ | cyclohexyl-H | — | F | H | H | |

-continued

| R | $-(A^1-Z^1)_m-$ | $-(A^2-Z^2)_n-$ | X | $L^1$ | $L^2$ | |
|---|---|---|---|---|---|---|
| n-C$_5$H$_{11}$ | cyclohexane(H) | — | F | H | F | |
| n-C$_5$H$_{11}$ | cyclohexane(H) | — | F | F | F | |
| n-C$_3$H$_7$ | cyclohexane(H) | — | Cl | H | H | |
| n-C$_3$H$_7$ | cyclohexane(H) | — | Cl | H | F | |
| n-C$_3$H$_7$ | cyclohexane(H) | — | Cl | F | F | |
| n-C$_5$H$_{11}$ | cyclohexane(H) | — | Cl | H | H | |
| n-C$_5$H$_{11}$ | cyclohexane(H) | — | Cl | H | F | |
| n-C$_5$H$_{11}$ | cyclohexane(H) | — | Cl | F | F | |
| n-C$_3$H$_7$ | cyclohexane(H) | — | OCF$_3$ | H | H | C 57 S$_B$ 70 N 82.9 I; $\Delta n = +0.109$; $\Delta\epsilon = 8.8$ |
| n-C$_3$H$_7$ | cyclohexane(H) | — | OCF$_3$ | H | F | |
| n-C$_3$H$_7$ | cyclohexane(H) | — | OCF$_3$ | F | F | |
| n-C$_5$H$_{11}$ | cyclohexane(H) | — | OCF$_3$ | H | H | |
| n-C$_5$H$_{11}$ | cyclohexane(H) | — | OCF$_3$ | H | F | |
| n-C$_5$H$_{11}$ | cyclohexane(H) | — | OCF$_3$ | F | F | |

-continued

| R | $-(A^1-Z^1)_m-$ | $-(A^2-Z^2)_n-$ | X | L¹ | L² |
|---|---|---|---|---|---|
| n-C₃H₇ | cyclohexyl(H) | — | CF₃ | H | H |
| n-C₃H₇ | cyclohexyl(H) | — | CF₃ | H | F |
| n-C₃H₇ | cyclohexyl(H) | — | CF₃ | F | F |
| n-C₅H₁₁ | cyclohexyl(H) | — | CF₃ | H | H |
| n-C₅H₁₁ | cyclohexyl(H) | — | CF₃ | H | F |
| n-C₅H₁₁ | cyclohexyl(H) | — | CF₃ | F | F |
| n-C₃H₇ | cyclohexyl(H) | — | OCH=CF₂ | H | H |
| n-C₃H₇ | cyclohexyl(H) | — | OCH=CF₂ | H | F |
| n-C₃H₇ | cyclohexyl(H) | — | OCH=CF₂ | F | F |
| n-C₅H₁₁ | cyclohexyl(H) | — | OCH=CF₂ | H | H |
| n-C₅H₁₁ | cyclohexyl(H) | — | OCH=CF₂ | H | F |
| n-C₅H₁₁ | cyclohexyl(H) | — | OCH=CF₂ | F | F |
| n-C₃H₇ | cyclohexyl(H) | — | OCH=CF₂ | H | H |
| n-C₃H₇ | cyclohexyl(H) | — | OCH=CF₂ | H | F |

-continued

| R | $-(A^1-Z^1)_m-$ | $-(A^2-Z^2)_n-$ | X | $L^1$ | $L^2$ |
|---|---|---|---|---|---|
| n-C$_3$H$_7$ | cyclohexyl-H | — | OCH=CF$_2$ | F | F |
| n-C$_5$H$_{11}$ | cyclohexyl-H | — | OCH=CF$_2$ | H | H |
| n-C$_5$H$_{11}$ | cyclohexyl-H | — | OCH=CF$_2$ | H | F |
| n-C$_5$H$_{11}$ | cyclohexyl-H | — | OCH=CF$_2$ | F | F |
| n-C$_3$H$_7$ | cyclohexyl-H | — | OC$_2$F$_5$ | H | H |
| n-C$_3$H$_7$ | cyclohexyl-H | — | OC$_2$F$_5$ | H | F |
| n-C$_3$H$_7$ | cyclohexyl-H | — | OC$_2$F$_5$ | F | F |
| n-C$_5$H$_{11}$ | cyclohexyl-H | — | OC$_3$F$_7$ | H | H |
| n-C$_5$H$_{11}$ | cyclohexyl-H | — | OC$_3$F$_7$ | H | F |
| n-C$_5$H$_{11}$ | cyclohexyl-H | — | OC$_3$F$_7$ | F | F |
| n-C$_3$H$_7$ | cyclohexyl-H | — | OCHFCF$_3$ | H | H |
| n-C$_3$H$_7$ | cyclohexyl-H | — | OCHFCF$_3$ | H | F |
| n-C$_3$H$_7$ | cyclohexyl-H | — | OCHFCF$_3$ | F | F |
| n-C$_5$H$_{11}$ | cyclohexyl-H | — | OCHFCF$_3$ | H | H |

-continued

| R | $-(A^1-Z^1)_m-$ | $-(A^2-Z^2)_n-$ | X | $L^1$ | $L^2$ |
|---|---|---|---|---|---|
| n-C$_5$H$_{11}$ | cyclohexyl(H) | — | OCHFCF$_3$ | H | F |
| n-C$_5$H$_{11}$ | cyclohexyl(H) | — | OCHFCF$_3$ | F | F |
| n-C$_3$H$_7$ | cyclohexyl(H) | — | OCHF$_2$ | H | H |
| n-C$_3$H$_7$ | cyclohexyl(H) | — | OCHF$_2$ | H | F |
| n-C$_3$H$_7$ | cyclohexyl(H) | — | OCHF$_2$ | F | F |
| n-C$_5$H$_{11}$ | cyclohexyl(H) | — | OCHF$_2$ | H | H |
| n-C$_5$H$_{11}$ | cyclohexyl(H) | — | OCHF$_2$ | H | F |
| n-C$_5$H$_{11}$ | cyclohexyl(H) | — | OCHF$_2$ | F | F |
| n-C$_3$H$_7$ | cyclohexyl(H) | — | F | H | H |
| n-C$_3$H$_7$ | cyclohexyl(H) | — | F | H | F |
| n-C$_3$H$_7$ | cyclohexyl(H) | — | F | F | F |
| n-C$_5$H$_{11}$ | cyclohexyl(H) | — | OCF$_3$ | H | H |
| n-C$_5$H$_{11}$ | cyclohexyl(H) | — | OCF$_3$ | H | F |
| n-C$_5$H$_{11}$ | cyclohexyl(H) | — | OCF$_3$ | F | F |

-continued
| R | $-(A^1-Z^1)_m-$ | $-(A^2-Z^2)_n-$ | X | $L^1$ | $L^2$ |
|---|---|---|---|---|---|
| C$_2$H$_5$ | — |  | F | H | H |
| C$_2$H$_5$ | — |  | F | H | F |
| C$_2$H$_5$ | — |  | F | F | F |
| n-C$_3$H$_7$ | — | 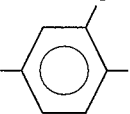 | F | H | H |
| n-C$_3$H$_7$ | — | 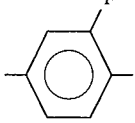 | F | H | F |
| n-C$_3$H$_7$ | — | 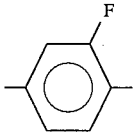 | F | F | F |
| n-C$_5$H$_{11}$ | — | 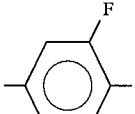 | F | H | H |
| n-C$_5$H$_{11}$ | — | 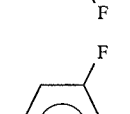 | F | H | F |
| n-C$_5$H$_{11}$ | — | 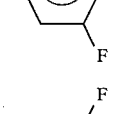 | F | F | F |
| OC$_2$H$_5$ | — | 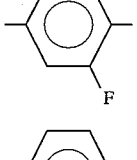 | F | H | H |
| OC$_2$H$_5$ | — | 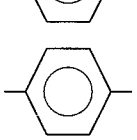 | F | H | F |

-continued

| R | $-(A^1-Z^1)_m-$ | $-(A^2-Z^2)_n-$ | X | L$^1$ | L$^2$ |
|---|---|---|---|---|---|
| OC$_2$H$_5$ | — | 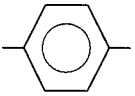 | F | F | F |
| OC$_3$H$_7$ | — |  | F | H | H |
| OC$_3$H$_7$ | — |  | F | H | F |
| OC$_3$H$_7$ | — |  | F | F | F |

Mixture examples

Example A

| PCH—5F | 9.0% | Clearing point [°C.]: | 87.4 |
|---|---|---|---|
| PCH—6F | 7.2% | Δn [589 nm, 20° C.]: | +0.0965 |
| PCH—7F | 5.4% | Δε [1 kHz, 20° C.]: | 5.62 |
| CCP—20CF$_3$ | 7.2% | ν$_{20}$ [mm$^2 \cdot$ s$^{-1}$]: | 13.99 |
| CCP—30CF$_3$ | 10.8% | | |
| CCP—40CF$_3$ | 8.1% | | |
| CCP—50CF$_3$ | 8.1% | | |
| BCH—3F.F | 10.8% | | |
| BCH—5F.F | 9.0% | | |
| ECCP—30CF$_3$ | 4.5% | | |
| ECCP—50CF$_3$ | 4.5% | | |
| CBC—33F | 1.8% | | |
| CBC—53F | 1.8% | | |
| CBC—55F | 1.8% | | |

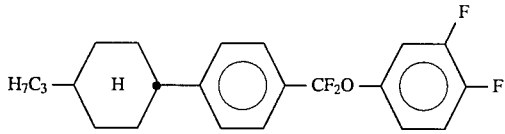 10.0%

Example B

Example C

| PCH—5F | 9.0% | Clearing point [°C.]: | 91.1 |
|---|---|---|---|
| PCH—6F | 7.2% | Δn [589 nm, 20° C.]: | +0.0978 |
| PCH—7F | 5.4% | Δε [1 kHz, 20° C.]: | 5.60 |
| CCP—20CF$_3$ | 7.2% | ν$_{20}$ [mm$^2 \cdot$ s$^{-1}$]: | 13.72 |
| CCP—30CF$_3$ | 10.8% | | |
| CCP—40CF$_3$ | 8.1% | | |
| CCP—50CF$_3$ | 8.1% | | |
| BCH—3F.F | 10.8% | | |
| BCH—5F.F | 9.0% | | |
| ECCP—30CF$_3$ | 4.5% | | |
| ECCP—50CF$_3$ | 4.5% | | |
| CBC—33F | 1.8% | | |
| CBC—53F | 1.8% | | |
| CBC—55F | 1.8% | | |

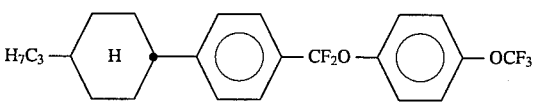 10.0%

| | | | |
|---|---|---|---|
| PCH—5F | 9.0% | Clearing point [°C.]: | 84.8 |
| PCH—6F | 7.2% | Δn [589 nm, 20° C.]: | +0.0965 |
| PCH—7F | 5.4% | Δε [1 kHz, 20° C.]: | 5.73 |
| CCP—20CF$_3$ | 7.2% | ν$_{20}$ [mm$^2$ · s$^{-1}$]: | 13.82 |
| CCP—30CF$_3$ | 10.8% | | |
| CCP—40CF$_3$ | 8.1% | | |
| CCP—50CF$_3$ | 8.1% | | |
| BCH—3F.F | 10.8% | | |
| BCH—5F.F | 9.0% | | |
| ECCP—30CF$_3$ | 4.5% | | |
| ECCP—50CF$_3$ | 4.5% | | |
| CBC—33F | 1.8% | | |
| CBC—53F | 1.8% | | |
| CBC—55F | 1.8% | | |

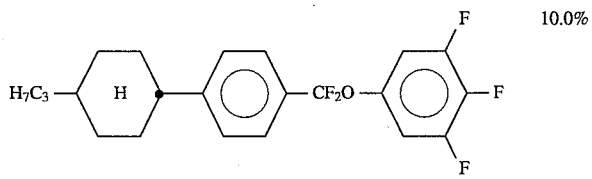

10.0%

Example D

| | | | |
|---|---|---|---|
| PCH—5F | 9.0% | Clearing point [°C.]: | 88.7 |
| PCH—6F | 7.2% | Δn [589 nm, 20° C.]: | +0.0974 |
| PCH—7F | 5.4% | Δε [1 kHz, 20° C.]: | 5.77 |
| CCP—20CF$_3$ | 7.2% | ν$_{20}$ [mm$^2$ · s$^{-1}$]: | 14.15 |
| CCP—30CF$_3$ | 10.8% | | |
| CCP—40CF$_3$ | 8.1% | | |
| CCP—50CF$_3$ | 8.1% | | |
| BCH—3F.F | 10.8% | | |
| BCH—5F.F | 9.0% | | |
| ECCP—30CF$_3$ | 4.5% | | |
| ECCP—50CF$_3$ | 4.5% | | |
| CBC—33F | 1.8% | | |
| CBC—53F | 1.8% | | |
| CBC—55F | 1.8% | | |

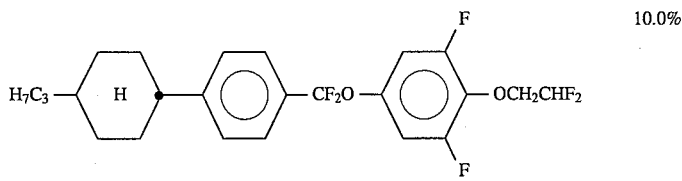

10.0%

Example E

| | | | |
|---|---|---|---|
| PCH—5F | 3.20% | Clearing point [C.]: | +109 |
| CCP—20CF$_2$.F.F | 17.04% | Δε [1 kHz. 20° C.]: | +8.2 |
| CCP—30CF$_2$.F.F | 16.00% | K$_3$/K$_1$: | 1.54 |
| CCP—50CF$_2$.F.F | 17.04% | V$_{(10.0.20)}$[V]: | 1.26 |
| CUP—2F.F | 5.36% | | |
| CUP—3F.F | 5.36% | | |
| CBC—33F | 5.36% | | |
| CBC—53F | 5.36% | | |
| CBC—55F | 5.28% | | |

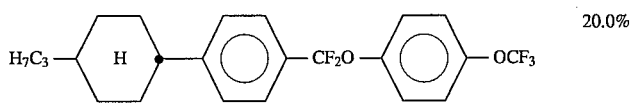

20.0%

Example F

| | | | |
|---|---|---|---|
| PCH—5F | 3.20% | Clearing point [C.]: | +110 |
| CCP—20CF₂.F.F | 17.04% | Δε [1 kHz. 20° C.]: | +9.0 |
| CCP—30CF₂.F.F | 16.00% | $K_3/K_1$: | 1.56 |
| CCP—50CF₂.F.F | 17.04% | $V_{(10.0.20)}[V]$: | 1.21 |
| CUP—2F.F | 5.36% | | |
| CUP—3F.F | 5.36% | | |
| CBC—33F | 5.36% | | |
| CBC—53F | 5.36% | | |
| CBC—55F | 5.28% | | |

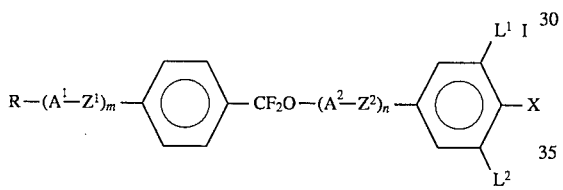

20.0%

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A benzene derivative of formula I

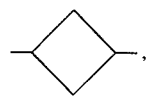

wherein

R is an alkyl or alkenyl radical having 1 to 15 carbon atoms which is optionally monosubstituted by CN or $CF_3$ or optionally at least monosubstituted by halogen, one or more $CH_2$ groups in these radicals optionally independently replaced by —O—, —S—, —CO—, —CO—O—, —O—CO— or —O—CO—O— that O atoms are not linked directly to one another, $A^1$ and $A^2$ are each independently (a) a trans-1,4-cyclohexylene radical in which one or more non-adjacent $CH_2$ groups is optionally replaced by —O— and/or —S—, (b) a 1,4-phenylene radical optionally monosubstituted or disubstituted by F or CN, and in which one or two CH groups is optionally replaced by N, (c) 1,4-cyclohexenylene, (d) a 1,4-bicyclo[2.2.2]octylene, piperidine-1,4-diyl, naphthalene-2,6-diyl, decahydro-naphthalene-2,6-diyl or 1,2,3,4-tetrahydronaphthelene-2,6-diyl radical, where the radicals (a) to (c) are optionally monosubstituted or polysubstituted by CN or fluorine, $Z^1$ and $Z^2$ are each independently —CO—O—, —O—CO—, —$CH_2$O—, —O$CH_2$—, —$CH_2CH_2$—, —CH=CH, —C≡C— or a single bond, or one of $Z^1$ and $Z^2$ is alternatively —$(CH_2)_4$— or —CH=CH—$CH_2CH_2$—, $L^1$ and $L^2$ are each independently H or F, m and n are each independently 0 or 1, and X is halogenated $C_{1-6}$-alkyl, $C_{1-6}$-alkoxy, $C_{2-6}$-alkenyl, F or Cl.

2. A compound according to claim 1 of formula I2

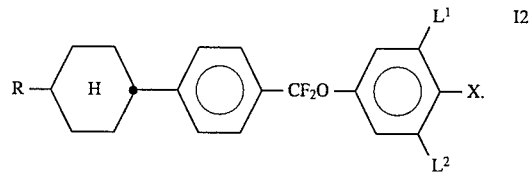

3. A compound of formula I according to claim 1, wherein X is F, Cl, $OCF_3$, $OCH_2CF_3$, $OCH_2CHF_2$, $OC_2F_5$, $OC_3F_7$, $OCHFCF_3$ or OCH=$CF_2$.

4. A compound according to claim 1, wherein $L^1$ and/or $L^2$ is fluorine.

5. A compound according to claim 2, wherein $L^1$ and/or $L^2$ is fluorine.

6. A compound according to claim 3, wherein $L^1$ and/or $L^2$ is fluorine.

7. A compound according to claim 1, of the formula

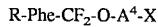

R-Phe-$CF_2$-O-$A^4$-X      Ia wherein Phe is a 1,4-phenylene radical and $A^4$ is

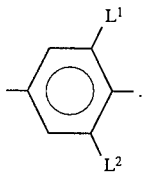

8. A compound according to claim 1, of the formulae

R-$A^1$-Phe-$CF_2$-O-$A^4$-X      Ib

R-$A^1$-$Z^1$-Phe-$CF_2$-O-$A^4$-X      Ic

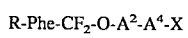

R-Phe-$CF_2$-O-$A^2$-$A^4$-X      Id or

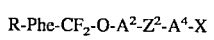

R-Phe-$CF_2$-O-$A^2$-$Z^2$-$A^4$-X      Ie wherein Phe is a 1,4-phenylene radical and $A^4$ is

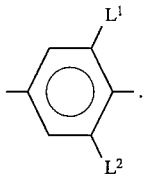

9. A compound according to claim 1, of the formulae

| | |
|---|---|
| R-A$^1$-Phe-CF$_2$-O-A$^2$-A$^4$-X | If |
| R-A$^1$-Z$^1$-Phe-CF$_2$-O-A$^2$-A$^4$-X | Ig |
| R-A$^1$-Z$^1$-Phe-CF$_2$-O-A$^2$-Z$^2$-A$^4$-X | Ih or |
| R-A$^1$-Phe-CF$_2$-O-A$^2$-Z$^2$-A$^4$-X | Ii | wherein Phe is a 1,4-phenylene radical and $A^4$ is

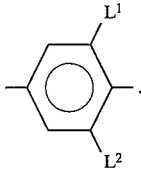

10. A compound according to claim 1, of the formulae

| | |
|---|---|
| R-Phe'-Z$^1$-Phe-CF$_2$-O-A$^4$-X | Ica |
| R-Cyc-Z$^1$-Phe-CF$_2$-A$^4$-X | Icb |
| R-Pyd-Z$^1$-Phe-CF$_2$-A$^4$-X | Icc |
| R-Pyr-Z$^1$-Phe-CF$_2$-A$^4$-X | Icd |
| R-Dio-Z$^1$-Phe-CF$_2$-A$^4$-X | Ice or |
| R-Phe-Z$^1$-Phe-CF$_2$-A$^4$-X | Icf | wherein Cyc is a 1,4-cyclohexylene radical, Che is a 1,4-cyclohexenylene radical, Dio is a 1,3-dioxane-2,5-diyl radical, Phe is a 1,4-phenylene radical, Phe' is a 1,4-phenylene radical optionally mono- or di-substituted by F or CN, Pyd is a pyridine-2,.5-diyl radical, Pyr is a pyrimidine-2,5-diyl radical, where Cyc may be unsubstituted or monosubstituted or disubstituted by F or CN, and $A^4$ is

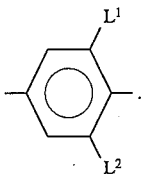

11. A compound according to claim 1, of the formulae

| | |
|---|---|
| R-Phe'-CF$_2$-O-Phe-Z$^2$-A$^4$-X | Iea |
| R-Phe'-CF$_2$-O-Cyc-Z$^2$-A$^4$-X | Ieb |
| R-Phe'-CF$_2$-O-Pyd-Z$^2$-A$^4$-X | Iec |
| R-Phe'-CF$_2$-O-Pyr-Z$^2$-A$^4$-X | Ied |
| R-Phe'-CF$_2$-O-Dio-Z$^2$-A$^4$-X | Ief or |
| R-Phe'-CF$_2$-O-Che-Z$^2$-A$^4$-X | Iee | wherein Cyc is a 1,4-cyclohexylene radical, Che is a 1,4-cyclohexenylene radical, Dio is a 1,3-dioxane-2,5-diyl radical, Phe is a 1,4-phenylene radical, Phe' is a 1,4-phenylene radical optionally mono- or di-substituted by F or CN, Pyd is a pyridine-2,5-diyl radical, Pyr is a pyrimidine-2,5-diyl radical, where Cyc may be unsubstituted or monosubstituted or disubstituted by F or CN, and $A^4$ is

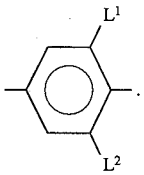

12. A liquid-crystalline medium comprising at least two liquid-crystalline components, wherein at least one component is at least one compound of the formula I according to claim 1.

13. A liquid-crystalline medium comprising at least two liquid-crystalline components, wherein at least one component is at least one compound of the formula I according to claim 2.

14. A liquid-crystal display element, comprising a liquid-crystalline medium according to claim 12.

15. A liquid-crystal display element, comprising a liquid-crystalline medium according to claim 13.

16. An electro-optical display element, containing a dielectric which is a liquid-crystalline medium according to claim 12.

17. An electro-optical display element, containing a dielectric which is a liquid-crystalline medium according to claim 13.

* * * * *